US011248225B2

United States Patent
(12) Wang et al.

(10) Patent No.: US 11,248,225 B2
(45) Date of Patent: Feb. 15, 2022

(54) GENE KNOCKOUT METHOD BASED ON BASE EDITING AND ITS APPLICATION

(71) Applicant: SUZHOU MAXIMUM BIO-TECH CO., LTD, Suzhou (CN)

(72) Inventors: Xiaoping Wang, Suzhou (CN); Xianjin Xu, Suzhou (CN); Huiying Liu, Suzhou (CN); Feng Zhang, Suzhou (CN)

(73) Assignee: SUZHOU MAXIMUM BIO-TECH CO., LTD, Suzhou (CN)

( * ) Notice: Subject to any disclaimer, the term of this patent is extended or adjusted under 35 U.S.C. 154(b) by 271 days.

(21) Appl. No.: 16/005,645

(22) Filed: Jun. 11, 2018

(65) Prior Publication Data

US 2020/0032240 A1 Jan. 30, 2020

(30) Foreign Application Priority Data

Jun. 12, 2017 (CN) ......................... 201710437122.0

(51) Int. Cl.

| | |
|---|---|
| ***C12N 15/00*** | (2006.01) |
| ***C12N 15/113*** | (2010.01) |
| ***C12N 15/10*** | (2006.01) |
| ***C12N 5/0783*** | (2010.01) |
| ***C12N 15/90*** | (2006.01) |

(52) U.S. Cl.

CPC ......... *C12N 15/102* (2013.01); *C12N 5/0636* (2013.01); *C12N 15/90* (2013.01)

(58) Field of Classification Search

CPC ..... C12N 15/102; C12N 5/0636; C12N 15/90

See application file for complete search history.

(56) References Cited

U.S. PATENT DOCUMENTS

2018/0237787 A1* 8/2018 Maianti ..................... A61P 9/10
2019/0185860 A1* 6/2019 Kim ....................... C12N 5/064

FOREIGN PATENT DOCUMENTS

GN 107164377 A 9/2017

OTHER PUBLICATIONS

Kuscu et al., "CRISPR-STOP: gene silencing through base-editing-induced nonsense mutations", Jun. 5, 2017, Nature Methods 14(7), p. 710-712.*

Kim et al., "Increasing the genome-targeting scope and precision of base editing with engineered Cas9-cytidine deaminase fusions" , epub Feb. 13, 2017, Nature Biotechnology 35(4), p. 371-376.*

CRISPR-STOP: gene silencing through base-editing-induced nonsense mutations, Cem Kuscu, Mahmut Parlak, Turan Tufan, Jiekun Yang, Karol Szlachta, Xiaolong Wei, Rashad Mammadov & Mazhar Adli, Brief Communications, Received Dec. 7, 2016; accepted May 2, 2017; published online Jun. 5, 2017; doi:10.1038/nmeth.4327.

Written Opinion of the International Searching Authority and Search Report, PCT/CN2018/088925, Form PCT/ISA/237 (Box No. V) (Jul. 2009).

Highly efficient RNA-guided base editing in mouse embryos, Kyoungmi Kim, Seuk-Min Ryu, Sang-Tae Kim, Gayoung Baek, Daesik Kim, Kayeong Lim, Eugene ChunG, Sunghyun Kim & Jin-Soo Kim, Brief Communications, Nature Bio Iechnology, Received Dec. 19, 2016; accepted Feb. 8, 2017; published online Feb. 27, 2017; doi:10.1038/nbt.3816.

* cited by examiner

*Primary Examiner* — Maria G Leavitt

(74) *Attorney, Agent, or Firm* — Flener IP & Business Law; Zareefa B. Flener

(57) ABSTRACT

Gene knockout method based on base editing and its application is provided. The gene knockout method comprises: selecting a 20 bp-NGG target sequence of the coding region of the gene to be knocked out, so that it contains a complete target codon CAA, CAG or CGA; and using sgRNA sequence to locate BE3 to the target sequence, to convert the target single-base C of the target codon into T and thus introduce a corresponding termination codon TAA, TAG orTGA in order to realize the knockout, wherein the target single-base C is located preferably on site 4-8 in the target sequence, the interval between the target codon and NGG is 12 to 14 bp, and the upstream base (H) near the target codon cannot be G; and the sgRNA sequence is a 20 bp sequence complementary to the target sequence.

1 Claim, 1 Drawing Sheet

Specification includes a Sequence Listing.

SEQUENCE LISTING

```
<160> NUMBER OF SEQ ID NOS: 28

<210> SEQ ID NO 1
<211> LENGTH: 7686
<212> TYPE: DNA
<213> ORGANISM: Artificial
<220> FEATURE:
<223> OTHER INFORMATION: Synthetic construct???rAPOBEC1-SaCas9-NLS-UGI-
      NLS

<400> SEQUENCE: 1

atatgccaag tacgcccccct attgacgtca atgacggtaa atggcccgcc tggcattatg      60

cccagtacat gaccttatgg gactttccta cttggcagta catctacgta ttagtcatcg     120

ctattaccat ggtgatgcgg ttttggcagt acatcaatgg gcgtggatag cggtttgact     180

cacggggatt tccaagtctc caccccattg acgtcaatgg gagtttgttt tggcaccaaa     240
```

-continued

```
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gagctcagag    420
actggcccag tggctgtgga ccccacattg agacggcgga tcgagcccca tgagtttgag    480
gtattcttcg atccgagaga gctccgcaag gagacctgcc tgctttacga aattaattgg    540
gggggccggc actccatttg gcgacataca tcacagaaca ctaacaagca cgtcgaagtc    600
aacttcatcg agaagttcac gacagaaaga tatttctgtc cgaacacaag gtgcagcatt    660
acctggtttc tcagctggag cccatgcggc gaatgtagta gggccatcac tgaattcctg    720
tcaaggtatc cccacgtcac tctgtttatt tacatcgcaa ggctgtacca ccacgctgac    780
ccccgcaatc gacaaggcct gcgggatttg atctcttcag gtgtgactat ccaaattatg    840
actgagcagg agtcaggata ctgctggaga aactttgtga attatagccc gagtaatgaa    900
gcccactggc ctaggtatcc ccatctgtgg gtacgactgt acgttcttga actgtactgc    960
atcatactgg gcctgcctcc ttgtctcaac attctgagaa ggaagcagcc acagctgaca   1020
ttctttacca tcgctcttca gtcttgtcat taccagcgac tgcccccaca cattctctgg   1080
gccaccgggt tgaaaagcgg cagcgagact cccgggacct cagagtccgc cacacccgaa   1140
agtaagcgga actatatcct cgggctggct attggcatca catctgtcgg ctatggtata   1200
atagactatg aaacaaggga cgtgattgac gcaggtgtga ggctgttcaa ggaggcaaac   1260
gtcgagaaca acgaaggtcg gagaagcaag aggggtgccc ggaggctgaa gaggaggaga   1320
aggcacagaa tacagcgggt caagaaactc ctgttcgact ataacctgct gaccgatcat   1380
tccgaactgt caggcatcaa tccttacgaa gccagagtca agggtctgtc tcaaaaactc   1440
tctgaggaag agttttccgc agccctgctg cacctggcta agaggagagg agtccacaac   1500
gtcaatgagg ttgaggagga tacagggaac gaactgtcta caaaggaaca gatcagccgg   1560
aatagcaagg ccctggaaga gaagtacgtt gctgaactgc agctggaaag gctcaagaaa   1620
gatggagagg ttcggggttc catcaacagg ttcaagacat ctgactatgt gaaggaagcc   1680
aagcaactgc tcaaggtgca gaaggcctac catcagctcg accagagctt cattgatact   1740
tacatagacc tgctggagac taggagaact tactacgaag ggcctggcga gggcagccct   1800
ttcggctgga aagatatcaa ggagtggtac gagatgctca tggggcattg cacctacttc   1860
cccgaagaac tgaggtcagt caagtacgcc tacaacgcag acctgtacaa cgccctgaat   1920
gatctcaaca atctcgtcat aactcgggat gaaaacgaga agctggaata ttatgagaag   1980
ttccagatta ttgaaaatgt gttcaaacag aagaagaaac ctaccctgaa acaaattgcc   2040
aaagagatcc tggtgaatga ggaggatatc aagggatatc gggttacttc taccggcaaa   2100
ccagagttca caaatctgaa agtttaccat gacatcaaag atattaccgc aagaaaggag   2160
atcatcgaga acgctgagct cctggaccag atcgctaaga ttctcactat ctatcagtcc   2220
agcgaggata ttcaggaaga gctgaccaac ctgaactcag agctgactca ggaagaaatc   2280
gaacaaatct ccaatctgaa aggatacact ggtacccata atctctcact caaggctatc   2340
aatctgatcc tggatgaact gtggcatact aacgacaatc agatcgccat cttcaatcgg   2400
ctcaaactgg tgcccaaaaa agtggacctg agccaacaga aagagattcc tacaaccctg   2460
gtggacgatt tcattctgag cccagtggtt aagcggagct tcatccaatc catcaaggtg   2520
atcaacgcta tcatcaagaa gtatggcctg cctaatgaca taatcattga actcgcaagg   2580
```

-continued

```
gaaaagaata gcaaagatgc ccagaagatg ataaacgaga tgcagaaacg gaacagacag   2640
actaacgaaa gaatcgagga aataatacgg accactggta aggagaacgc taagtatctg   2700
atcgagaaaa tcaagctgca cgatatgcag gaaggcaagt gcctgtattc tctggaggct   2760
atacccctgg aggatctgct caataatcct ttcaattacg aggtggatca catcatacca   2820
agatccgtga gctttgacaa tagctttaat aataaggtgc tcgtgaagca ggaggaaaac   2880
tcaaagaaag gcaacaggac cccattccag tacctgtcca gctctgacag caagattagc   2940
tacgaaacct tcaagaaaca catcctgaat ctggccaagg gcaagggaag aataagcaaa   3000
acaaagaaag agtatctcct ggaggaaagg gacatcaaca ggttttcagt gcagaaagat   3060
tttatcaatc ggaatctcgt tgacacaaga tatgctacca gagggctcat gaatctgctc   3120
aggtcatact ttagggtgaa caacctggat gtgaaggtca aatccataaa tggagggttc   3180
acttcctttc tcaggagaaa atggaagttt aagaaagaga gaaataaggg ttacaaacat   3240
cacgccgagg acgcactgat cattgccaac gctgacttta tctttaagga atggaagaag   3300
ctggacaaag caaagaaggt gatggagaat cagatgtttg aggaaaagca ggccgagtct   3360
atgcctgaga ttgaaacaga gcaggaatac aaagagatct tcattactcc acatcagatt   3420
aagcacatca aggactttaa ggactataaa tactcacata gggtggataa gaaacctaat   3480
agagagctga tcaacgatac actctactca acaaggaaag acgacaaagg aaacaccctg   3540
attgttaata atctcaatgg gctgtatgac aaagataatg acaagctgaa gaaactcatc   3600
aacaagtccc cagaaaagct gctgatgtat caccacgatc cccaaacata tcagaagctg   3660
aagctgatta tggagcagta tggtgatgag aagaaccctc tgtacaagta ctatgaagag   3720
acagggaact acctcactaa gtacagcaag aaagacaacg gacccgttat caagaagatc   3780
aagtactacg gcaataagct gaacgcccac ctggatatca cagatgacta tccaaactct   3840
aggaacaaag tggtgaaact gtccctgaag ccatacagat ttgatgtgta tctggataac   3900
ggagtctata agttcgtcac agtcaagaac ctggacgtca tcaagaagga gaattactat   3960
gaagtgaaca gcaaatgcta cgaggaagcc aagaagctca agaagatttc taaccaggca   4020
gagtttatcg cctctttcta caataacgat ctgatcaaga tcaacggaga actgtacaga   4080
gtgatcggcg tgaataatga cctcctgaat aggatcgagg ttaacatgat cgatatcaca   4140
tatcgggagt acctggagaa tatgaatgac aagaggcctc ccagaattat caagactatt   4200
gccagcaaaa cccaatctat aaaaaagtac tcaacagata tcctggggaa cctgtatgag   4260
gtgaagtcaa agaagcatcc ccagattatc aagaaaggcg gcagccccaa gaagaagagg   4320
aaggtgagca gcgactacaa ggaccacgac ggcgactaca aggaccacga catcgactac   4380
aaggacgacg acgacaagtc tggtggttct actaatctgt cagatattat tgaaaaggag   4440
accggtaagc aactggttat ccaggaatcc atcctcatgc tcccagagga ggtggaagaa   4500
gtcattggga acaagccgga aagcgatata ctcgtgcaca ccgcctacga cgagagcacc   4560
gacgagaatg tcatgcttct gactagcgac gcccctgaat acaagccttg ggctctggtc   4620
atacaggata gcaacggtga gaacaagatt aagatgctct ctggtggttc tcccaagaag   4680
aagaggaaag tctaaccggt catcatcacc atcaccattg agtttaaacc cgctgatcag   4740
cctcgactgt gccttctagt tgccagccat ctgttgtttg cccctccccc gtgccttcct   4800
tgaccctgga aggtgccact cccactgtcc tttcctaata aaatgaggaa attgcatcgc   4860
attgtctgag taggtgtcat tctattctgg ggggtggggt ggggcaggac agcaaggggg   4920
aggattggga agacaatagc aggcatgctg gggatgcggt gggctctatg gcttctgagg   4980
```

```
cggaaagaac cagctggggc tcgataccgt cgacctctag ctagagcttg gcgtaatcat   5040
ggtcatagct gtttcctgtg tgaaattgtt atccgctcac aattccacac aacatacgag   5100
ccggaagcat aaagtgtaaa gcctagggtg cctaatgagt gagctaactc acattaattg   5160
cgttgcgctc actgcccgct ttccagtcgg gaaacctgtc gtgccagctg cattaatgaa   5220
tcggccaacg cgcggggaga ggcggtttgc gtattgggcg ctcttccgct tcctcgctca   5280
ctgactcgct gcgctcggtc gttcggctgc ggcgagcggt atcagctcac tcaaaggcgg   5340
taatacggtt atccacagaa tcaggggata acgcaggaaa gaacatgtga gcaaaaggcc   5400
agcaaaaggc caggaaccgt aaaaaggccg cgttgctggc gtttttccat aggctccgcc   5460
cccctgacga gcatcacaaa aatcgacgct caagtcagag gtggcgaaac ccgacaggac   5520
tataaagata ccaggcgttt ccccctggaa gctccctcgt gcgctctcct gttccgaccc   5580
tgccgcttac cggatacctg tccgcctttc tcccttcggg aagcgtggcg ctttctcata   5640
gctcacgctg taggtatctc agttcggtgt aggtcgttcg ctccaagctg ggctgtgtgc   5700
acgaaccccc cgttcagccc gaccgctgcg ccttatccgg taactatcgt cttgagtcca   5760
acccggtaag acacgactta tcgccactgg cagcagccac tggtaacagg attagcagag   5820
cgaggtatgt aggcggtgct acagagttct tgaagtggtg gcctaactac ggctacacta   5880
gaagaacagt atttggtatc tgcgctctgc tgaagccagt taccttcgga aaaagagttg   5940
gtagctcttg atccggcaaa caaaccaccg ctggtagcgg tggttttttt gtttgcaagc   6000
agcagattac gcgcagaaaa aaaggatctc aagaagatcc tttgatcttt tctacggggt   6060
ctgacgctca gtggaacgaa aactcacgtt aagggatttt ggtcatgaga ttatcaaaaa   6120
ggatcttcac ctagatcctt ttaaattaaa aatgaagttt taaatcaatc taaagtatat   6180
atgagtaaac ttggtctgac agttaccaat gcttaatcag tgaggcacct atctcagcga   6240
tctgtctatt tcgttcatcc atagttgcct gactccccgt cgtgtagata actacgatac   6300
gggagggctt accatctggc cccagtgctg caatgatacc gcgagaccca cgctcaccgg   6360
ctccagattt atcagcaata aaccagccag ccggaagggc cgagcgcaga agtggtcctg   6420
caactttatc cgcctccatc cagtctatta attgttgccg ggaagctaga gtaagtagtt   6480
cgccagttaa tagtttgcgc aacgttgttg ccattgctac aggcatcgtg gtgtcacgct   6540
cgtcgtttgg tatggcttca ttcagctccg gttcccaacg atcaaggcga gttacatgat   6600
cccccatgtt gtgcaaaaaa gcggttagct ccttcggtcc tccgatcgtt gtcagaagta   6660
agttggccgc agtgttatca ctcatggtta tggcagcact gcataattct cttactgtca   6720
tgccatccgt aagatgcttt tctgtgactg gtgagtactc aaccaagtca ttctgagaat   6780
agtgtatgcg gcgaccgagt tgctcttgcc cggcgtcaat acgggataat accgcgccac   6840
atagcagaac tttaaaagtg ctcatcattg gaaaacgttc ttcggggcga aaactctcaa   6900
ggatcttacc gctgttgaga tccagttcga tgtaacccac tcgtgcaccc aactgatctt   6960
cagcatcttt tactttcacc agcgtttctg ggtgagcaaa aacaggaagg caaaatgccg   7020
caaaaaaggg aataagggcg acacggaaat gttgaatact catactcttc ctttttcaat   7080
attattgaag catttatcag ggttattgtc tcatgagcgg atacatattt gaatgtattt   7140
agaaaaataa acaaataggg gttccgcgca catttccccg aaaagtgcca cctgacgtcg   7200
acggatcggg agatcgatct cccgatcccc tagggtcgac tctcagtaca atctgctctg   7260
atgccgcata gttaagccag tatctgctcc ctgcttgtgt gttggaggtc gctgagtagt   7320
```

```
gcgcgagcaa aatttaagct acaacaaggc aaggcttgac cgacaattgc atgaagaatc   7380

tgcttagggt taggcgtttt gcgctgcttc gcgatgtacg ggccagatat acgcgttgac   7440

attgattatt gactagttat taatagtaat caattacggg gtcattagtt catagcccat   7500

atatggagtt ccgcgttaca taacttacgg taaatggccc gcctggctga ccgcccaacg   7560

acccccgccc attgacgtca ataatgacgt atgttcccat agtaacgcca atagggactt   7620

tccattgacg tcaatgggtg gagtatttac ggtaaactgc ccacttggca gtacatcaag   7680

tgtatc                                                              7686
```

<210> SEQ ID NO 2
<211> LENGTH: 8670
<212> TYPE: DNA
<213> ORGANISM: Artificial
<220> FEATURE:
<223> OTHER INFORMATION: Synthetic construct???3xUGI-rAPOBEC1-SaCas9-
      NLS-UGI-NLS

<400> SEQUENCE: 2

```
atatgccaag tacgccccct attgacgtca atgacggtaa atggcccgcc tggcattatg     60

cccagtacat gaccttatgg gactttccta cttggcagta catctacgta ttagtcatcg    120

ctattaccat ggtgatgcgg ttttggcagt acatcaatgg gcgtggatag cggtttgact    180

cacggggatt tccaagtctc caccccattg acgtcaatgg gagtttgttt tggcaccaaa    240

atcaacggga ctttccaaaa tgtcgtaaca actccgcccc attgacgcaa atgggcggta    300

ggcgtgtacg gtgggaggtc tatataagca gagctggttt agtgaaccgt cagatccgct    360

agagatccgc ggccgctaat acgactcact atagggagag ccgccaccgg gcccatgact    420

aatctgtcag atattattga aaaggagacc ggtaagcaac tggttatcca ggaatccatc    480

ctcatgctcc cagaggaggt ggaagaagtc attgggaaca agccggaaag cgatatactc    540

gtgcacaccg cctacgacga gagcaccgac gagaatgtca tgcttctgac tagcgacgcc    600

cctgaataca agccttgggc tctggtcata caggatagca acggtgagaa caagattaag    660

atgctcccca agaagaagag gaaagtcgag ggcagaggaa gtctgctaac atgcggtgac    720

gtcgaggaga atcctggccc aaccaacctg tccgatatca ttgagaaaga gaccggcaaa    780

cagctggtga tccaggagag catcctgatg ctgcccgaag aggtggagga agtgatcggc    840

aacaagcccg agtccgacat cctggtgcac acagcctatg atgaatccac cgacgagaac    900

gtgatgctgc tgacctccga tgctcccgag tataaaccct gggcactggt gatccaggac    960

tctaatggag agaacaagat caagatgctg cccaagaaga agaggaaagt cgctactaac   1020

ttcagcctgc tgaagcaggc tggagacgtg gaggagaacc ctggacctac aaacctcagt   1080

gacattatcg agaaggaaac aggaaaacag ctcgtcattc aagaatctat tcttatgttg   1140

cctgaggaag tcgaagaggt tattggcaat aaacctgaat ctgatattct tgtccatacc   1200

gcttacgatg agtccacaga tgaaaatgtt atgctgctca catctgacgc accagagtac   1260

aaaccatggg cgctcgttat tcaagattcc aacggcgaaa acaaaatcaa aatgcttccc   1320

aagaagaaga ggaaagtcga aggacggggc tccctcctga cctgtggcga tgtggaagag   1380

aaccccggcc ccatgagctc agagactggc ccagtggctg tggaccccac attgagacgg   1440

cggatcgagc cccatgagtt tgaggtattc ttcgatccga gagagctccg caaggagacc   1500

tgcctgcttt acgaaattaa ttgggggggc cggcactcca tttggcgaca tacatcacag   1560

aacactaaca agcacgtcga agtcaacttc atcgagaagt tcacgacaga aagatatttc   1620
```

-continued

```
tgtccgaaca caaggtgcag cattacctgg tttctcagct ggagcccatg cggcgaatgt   1680
agtagggcca tcactgaatt cctgtcaagg tatccccacg tcactctgtt tatttacatc   1740
gcaaggctgt accaccacgc tgacccccgc aatcgacaag gcctgcggga tttgatctct   1800
tcaggtgtga ctatccaaat tatgactgag caggagtcag gatactgctg gagaaacttt   1860
gtgaattata gcccgagtaa tgaagcccac tggcctaggt atccccatct gtgggtacga   1920
ctgtacgttc ttgaactgta ctgcatcata ctgggcctgc ctccttgtct caacattctg   1980
agaaggaagc agccacagct gacattcttt accatcgctc ttcagtcttg tcattaccag   2040
cgactgcccc cacacattct ctgggccacc gggttgaaaa gcggcagcga gactcccggg   2100
acctcagagt ccgccacacc cgaaagtaag cggaactata tcctcgggct ggctattggc   2160
atcacatctg tcggctatgg tataatagac tatgaaacaa gggacgtgat tgacgcaggt   2220
gtgaggctgt tcaaggaggc aaacgtcgag aacaacgaag gtcggagaag caagaggggt   2280
gcccggaggc tgaagaggag gagaaggcac agaatacagc gggtcaagaa actcctgttc   2340
gactataacc tgctgaccga tcattccgaa ctgtcaggca tcaatcctta cgaagccaga   2400
gtcaagggtc tgtctcaaaa actctctgag gaagagtttt ccgcagccct gctgcacctg   2460
gctaagagga gaggagtcca caacgtcaat gaggttgagg aggatacagg gaacgaactg   2520
tctacaaagg aacagatcag ccggaatagc aaggccctgg aagagaagta cgttgctgaa   2580
ctgcagctgg aaaggctcaa gaaagatgga gaggttcggg gttccatcaa caggttcaag   2640
acatctgact atgtgaagga agccaagcaa ctgctcaagg tgcagaaggc ctaccatcag   2700
ctcgaccaga gcttcattga tacttacata gacctgctgg agactaggag aacttactac   2760
gaagggcctg gcgagggcag ccctttcggc tggaaagata tcaaggagtg gtacgagatg   2820
ctcatggggc attgcaccta cttccccgaa gaactgaggt cagtcaagta cgcctacaac   2880
gcagacctgt acaacgccct gaatgatctc aacaatctcg tcataactcg ggatgaaaac   2940
gagaagctgg aatattatga gaagttccag attattgaaa atgtgttcaa acagaagaag   3000
aaacctaccc tgaaacaaat tgccaaagag atcctggtga atgaggagga tatcaaggga   3060
tatcgggtta cttctaccgg caaaccagag ttcacaaatc tgaaagttta ccatgacatc   3120
aaagatatta ccgcaagaaa ggagatcatc gagaacgctg agctcctgga ccagatcgct   3180
aagattctca ctatctatca gtccagcgag gatattcagg aagagctgac caacctgaac   3240
tcagagctga ctcaggaaga aatcgaacaa atctccaatc tgaaaggata cactggtacc   3300
cataatctct cactcaaggc tatcaatctg atcctggatg aactgtggca tactaacgac   3360
aatcagatcg ccatcttcaa tcggctcaaa ctggtgccca aaaaagtgga cctgagccaa   3420
cagaaagaga ttcctacaac cctggtggac gatttcattc tgagcccagt ggttaagcgg   3480
agcttcatcc aatccatcaa ggtgatcaac gctatcatca agaagtatgg cctgcctaat   3540
gacataatca ttgaactcgc aagggaaaag aatagcaaag atgcccagaa gatgataaac   3600
gagatgcaga aacggaacag acagactaac gaaagaatcg aggaaataat acggaccact   3660
ggtaaggaga acgctaagta tctgatcgag aaaatcaagc tgcacgatat gcaggaaggc   3720
aagtgcctgt attctctgga ggctataccc ctggaggatc tgctcaataa tcctttcaat   3780
tacgaggtgg atcacatcat accaagatcc gtgagctttg acaatagctt taataataag   3840
gtgctcgtga agcaggagga aaactcaaag aaaggcaaca ggaccccatt ccagtacctg   3900
tccagctctg acagcaagat tagctacgaa accttcaaga aacacatcct gaatctggcc   3960
aagggcaagg gaagaataag caaaacaaag aaagagtatc tcctggagga aagggacatc   4020
```

```
aacaggtttt cagtgcagaa agattttatc aatcggaatc tcgttgacac aagatatgct   4080
accagagggc tcatgaatct gctcaggtca tactttaggg tgaacaacct ggatgtgaag   4140
gtcaaatcca taaatggagg gttcacttcc tttctcagga gaaaatggaa gtttaagaaa   4200
gagagaaata agggttacaa acatcacgcc gaggacgcac tgatcattgc caacgctgac   4260
tttatcttta aggaatggaa gaagctggac aaagcaaaga aggtgatgga gaatcagatg   4320
tttgaggaaa agcaggccga gtctatgcct gagattgaaa cagagcagga atacaaagag   4380
atcttcatta ctccacatca gattaagcac atcaaggact ttaaggacta taaatactca   4440
catagggtgg ataagaaacc taatagagag ctgatcaacg atacactcta ctcaacaagg   4500
aaagacgaca aaggaaacac cctgattgtt aataatctca atgggctgta tgacaaagat   4560
aatgacaagc tgaagaaact catcaacaag tccccagaaa agctgctgat gtatcaccac   4620
gatccccaaa catatcagaa gctgaagctg attatggagc agtatggtga tgagaagaac   4680
cctctgtaca agtactatga agagacaggg aactacctca ctaagtacag caagaaagac   4740
aacggacccg ttatcaagaa gatcaagtac tacggcaata agctgaacgc ccacctggat   4800
atcacagatg actatccaaa ctctaggaac aaagtggtga aactgtccct gaagccatac   4860
agatttgatg tgtatctgga taacggagtc tataagttcg tcacagtcaa gaacctggac   4920
gtcatcaaga aggagaatta ctatgaagtg aacagcaaat gctacgagga agccaagaag   4980
ctcaagaaga tttctaacca ggcagagttt atcgcctctt tctacaataa cgatctgatc   5040
aagatcaacg gagaactgta cagagtgatc ggcgtgaata atgacctcct gaataggatc   5100
gaggttaaca tgatcgatat cacatatcgg gagtacctgg agaatatgaa tgacaagagg   5160
cctcccagaa ttatcaagac tattgccagc aaaacccaat ctataaaaaa gtactcaaca   5220
gatatcctgg ggaacctgta tgaggtgaag tcaaagaagc atccccagat tatcaagaaa   5280
ggcggcagcc ccaagaagaa gaggaaggtg agcagcgact acaaggacca cgacggcgac   5340
tacaaggacc acgacatcga ctacaaggac gacgacgaca agtctggtgg ttctactaat   5400
ctgtcagata ttattgaaaa ggagaccggt aagcaactgg ttatccagga atccatcctc   5460
atgctcccag aggaggtgga agaagtcatt gggaacaagc cggaaagcga tatactcgtg   5520
cacaccgcct acgacgagag caccgacgag aatgtcatgc ttctgactag cgacgcccct   5580
gaatacaagc cttgggctct ggtcatacag gatagcaacg gtgagaacaa gattaagatg   5640
ctctctggtg gttctcccaa gaagaagagg aaagtctaac cggtcatcat caccatcacc   5700
attgagttta aacccgctga tcagcctcga ctgtgccttc tagttgccag ccatctgttg   5760
tttgcccctc ccccgtgcct tccttgaccc tggaaggtgc cactcccact gtcctttcct   5820
aataaaatga ggaaattgca tcgcattgtc tgagtaggtg tcattctatt ctggggggtg   5880
gggtggggca ggacagcaag ggggaggatt gggaagacaa tagcaggcat gctggggatg   5940
cggtgggctc tatggcttct gaggcggaaa gaaccagctg gggctcgata ccgtcgacct   6000
ctagctagag cttggcgtaa tcatggtcat agctgtttcc tgtgtgaaat tgttatccgc   6060
tcacaattcc acacaacata cgagccggaa gcataaagtg taaagcctag ggtgcctaat   6120
gagtgagcta actcacatta attgcgttgc gctcactgcc cgctttccag tcgggaaacc   6180
tgtcgtgcca gctgcattaa tgaatcggcc aacgcgcggg gagaggcggt ttgcgtattg   6240
ggcgctcttc cgcttcctcg ctcactgact cgctgcgctc ggtcgttcgg ctgcggcgag   6300
cggtatcagc tcactcaaag gcggtaatac ggttatccac agaatcaggg gataacgcag   6360
```

-continued

```
gaaagaacat gtgagcaaaa ggccagcaaa aggccaggaa ccgtaaaaag gccgcgttgc   6420
tggcgttttt ccataggctc cgcccccctg acgagcatca caaaaatcga cgctcaagtc   6480
agaggtggcg aaacccgaca ggactataaa gataccaggc gtttccccct ggaagctccc   6540
tcgtgcgctc tcctgttccg accctgccgc ttaccggata cctgtccgcc tttctccctt   6600
cgggaagcgt ggcgctttct catagctcac gctgtaggta tctcagttcg gtgtaggtcg   6660
ttcgctccaa gctgggctgt gtgcacgaac cccccgttca gcccgaccgc tgcgccttat   6720
ccggtaacta tcgtcttgag tccaacccgg taagacacga cttatcgcca ctggcagcag   6780
ccactggtaa caggattagc agagcgaggt atgtaggcgg tgctacagag ttcttgaagt   6840
ggtggcctaa ctacggctac actagaagaa cagtatttgg tatctgcgct ctgctgaagc   6900
cagttacctt cggaaaaaga gttggtagct cttgatccgg caaacaaacc accgctggta   6960
gcggtggttt ttttgtttgc aagcagcaga ttacgcgcag aaaaaaagga tctcaagaag   7020
atcctttgat cttttctacg gggtctgacg ctcagtggaa cgaaaactca cgttaaggga   7080
ttttggtcat gagattatca aaaaggatct tcacctagat ccttttaaat taaaaatgaa   7140
gttttaaatc aatctaaagt atatatgagt aaacttggtc tgacagttac caatgcttaa   7200
tcagtgaggc acctatctca gcgatctgtc tatttcgttc atccatagtt gcctgactcc   7260
ccgtcgtgta gataactacg atacgggagg gcttaccatc tggccccagt gctgcaatga   7320
taccgcgaga cccacgctca ccggctccag atttatcagc aataaaccag ccagccggaa   7380
gggccgagcg cagaagtggt cctgcaactt tatccgcctc catccagtct attaattgtt   7440
gccgggaagc tagagtaagt agttcgccag ttaatagttt gcgcaacgtt gttgccattg   7500
ctacaggcat cgtggtgtca cgctcgtcgt ttggtatggc ttcattcagc tccggttccc   7560
aacgatcaag gcgagttaca tgatccccca tgttgtgcaa aaaagcggtt agctccttcg   7620
gtcctccgat cgttgtcaga agtaagttgg ccgcagtgtt atcactcatg gttatggcag   7680
cactgcataa ttctcttact gtcatgccat ccgtaagatg cttttctgtg actggtgagt   7740
actcaaccaa gtcattctga gaatagtgta tgcggcgacc gagttgctct tgcccggcgt   7800
caatacggga taataccgcg ccacatagca gaactttaaa agtgctcatc attggaaaac   7860
gttcttcggg gcgaaaactc tcaaggatct taccgctgtt gagatccagt tcgatgtaac   7920
ccactcgtgc acccaactga tcttcagcat cttttacttt caccagcgtt tctgggtgag   7980
caaaaacagg aaggcaaaat gccgcaaaaa agggaataag ggcgacacgg aaatgttgaa   8040
tactcatact cttccttttt caatattatt gaagcattta tcagggttat tgtctcatga   8100
gcggatacat atttgaatgt atttagaaaa ataaacaaat aggggttccg cgcacatttc   8160
cccgaaaagt gccacctgac gtcgacggat cgggagatcg atctcccgat cccctagggt   8220
cgactctcag tacaatctgc tctgatgccg catagttaag ccagtatctg ctccctgctt   8280
gtgtgttgga ggtcgctgag tagtgcgcga gcaaaattta agctacaaca aggcaaggct   8340
tgaccgacaa ttgcatgaag aatctgctta gggttaggcg ttttgcgctg cttcgcgatg   8400
tacgggccag atatacgcgt tgacattgat tattgactag ttattaatag taatcaatta   8460
cggggtcatt agttcatagc ccatatatgg agttccgcgt tacataactt acggtaaatg   8520
gcccgcctgg ctgaccgccc aacgaccccc gcccattgac gtcaataatg acgtatgttc   8580
ccatagtaac gccaataggg actttccatt gacgtcaatg ggtggagtat ttacggtaaa   8640
ctgcccactt ggcagtacat caagtgtatc                                    8670
```

<210> SEQ ID NO 3
<211> LENGTH: 8532
<212> TYPE: DNA
<213> ORGANISM: Artificial
<220> FEATURE:
<223> OTHER INFORMATION: Synthetic construct???rAPOBEC1-SpCas9-NLS-UGI-
NLS

<400> SEQUENCE: 3

```
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gagctcagag    420
actggcccag tggctgtgga ccccacattg agacggcgga tcgagcccca tgagtttgag    480
gtattcttcg atccgagaga gctccgcaag gagacctgcc tgctttacga aattaattgg    540
gggggccggc actccatttg gcgacataca tcacagaaca ctaacaagca cgtcgaagtc    600
aacttcatcg agaagttcac gacagaaaga tatttctgtc cgaacacaag gtgcagcatt    660
acctggtttc tcagctggag cccatgcggc gaatgtagta gggccatcac tgaattcctg    720
tcaaggtatc cccacgtcac tctgtttatt tacatcgcaa ggctgtacca ccacgctgac    780
ccccgcaatc gacaaggcct gcgggatttg atctcttcag gtgtgactat ccaaattatg    840
actgagcagg agtcaggata ctgctggaga aactttgtga attatagccc gagtaatgaa    900
gcccactggc ctaggtatcc ccatctgtgg gtacgactgt acgttcttga actgtactgc    960
atcatactgg gcctgcctcc ttgtctcaac attctgagaa ggaagcagcc acagctgaca   1020
ttctttacca tcgctcttca gtcttgtcat taccagcgac tgccccccaca cattctctgg   1080
gccaccgggt tgaaaagcgg cagcgagact cccgggacct cagagtccgc cacacccgaa   1140
agtgataaaa agtattctat tggtttagcc atcggcacta attccgttgg atgggctgtc   1200
ataaccgatg aatacaaagt accttcaaag aaatttaagg tgttggggaa cacagaccgt   1260
cattcgatta aaaagaatct tatcggtgcc ctcctattcg atagtggcga aacggcagag   1320
gcgactcgcc tgaaacgaac cgctcggaga aggtatacac gtcgcaagaa ccgaatatgt   1380
tacttacaag aaatttttag caatgagatg gccaaagttg acgattcttt ctttcaccgt   1440
ttggaagagt ccttccttgt cgaagaggac aagaaacatg aacggcaccc catctttgga   1500
aacatagtag atgaggtggc atatcatgaa aagtacccaa cgatttatca cctcagaaaa   1560
aagctagttg actcaactga taaagcggac ctgaggttaa tctacttggc tcttgcccat   1620
atgataaagt tccgtgggca ctttctcatt gagggtgatc taaatccgga caactcggat   1680
gtcgacaaac tgttcatcca gttagtacaa acctataatc agttgtttga agagaaccct   1740
ataaatgcaa gtggcgtgga tgcgaaggct attcttagcg cccgcctctc taaatcccga   1800
cggctagaaa acctgatcgc acaattaccc ggagagaaga aaaatgggtt gttcggtaac   1860
cttatagcgc tctcactagg cctgacacca aattttaagt cgaacttcga cttagctgaa   1920
gatgccaaat tgcagcttag taaggacacg tacgatgacg atctcgacaa tctactggca   1980
caaattggag atcagtatgc ggacttattt ttggctgcca aaaaccttag cgatgcaatc   2040
ctcctatctg acatactgag agttaatact gagattacca aggcgccgtt atccgcttca   2100
```

```
atgatcaaaa ggtacgatga acatcaccaa gacttgacac ttctcaaggc cctagtccgt   2160
cagcaactgc ctgagaaata taaggaaata ttctttgatc agtcgaaaaa cgggtacgca   2220
ggttatattg acggcggagc gagtcaagag gaattctaca agtttatcaa acccatatta   2280
gagaagatgg atgggacgga agagttgctt gtaaaactca atcgcgaaga tctactgcga   2340
aagcagcgga ctttcgacaa cggtagcatt ccacatcaaa tccacttagg cgaattgcat   2400
gctatactta gaaggcagga ggatttttat ccgttcctca aagacaatcg tgaaaagatt   2460
gagaaaatcc taacctttcg cataccttac tatgtgggac ccctggcccg agggaactct   2520
cggttcgcat ggatgacaag aaagtccgaa gaaacgatta ctccatggaa ttttgaggaa   2580
gttgtcgata aaggtgcgtc agctcaatcg ttcatcgaga ggatgaccaa ctttgacaag   2640
aatttaccga acgaaaaagt attgcctaag cacagtttac tttacgagta tttcacagtg   2700
tacaatgaac tcacgaaagt taagtatgtc actgagggca tgcgtaaacc cgcctttcta   2760
agcggagaac agaagaaagc aatagtagat ctgttattca agaccaaccg caaagtgaca   2820
gttaagcaat tgaaagagga ctactttaag aaaattgaat gcttcgattc tgtcgagatc   2880
tccggggtag aagatcgatt taatgcgtca cttggtacgt atcatgacct cctaaagata   2940
attaaagata aggacttcct ggataacgaa gagaatgaag atatcttaga agatatagtg   3000
ttgactctta ccctctttga agatcgggaa atgattgagg aaagactaaa aacatacgct   3060
cacctgttcg acgataaggt tatgaaacag ttaaagaggc gtcgctatac gggctgggga   3120
cgattgtcgc ggaaacttat caacgggata agagacaagc aaagtggtaa aactattctc   3180
gattttctaa agagcgacgg cttcgccaat aggaacttta tgcagctgat ccatgatgac   3240
tctttaacct tcaaagagga tatacaaaag gcacaggttt ccggacaagg ggactcattg   3300
cacgaacata ttgcgaatct tgctggttcg ccagccatca aaaagggcat actccagaca   3360
gtcaaagtag tggatgagct agttaaggtc atgggacgtc acaaaccgga aaacattgta   3420
atcgagatgg cacgcgaaaa tcaaacgact cagaaggggc aaaaaaacag tcgagagcgg   3480
atgaagagaa tagaagaggg tattaaagaa ctgggcagcc agatcttaaa ggagcatcct   3540
gtggaaaata cccaattgca gaacgagaaa ctttacctct attacctaca aaatggaagg   3600
gacatgtatg ttgatcagga actggacata aaccgtttat ctgattacga cgtcgatcac   3660
attgtacccc aatccttttt gaaggacgat tcaatcgaca ataaagtgct tacacgctcg   3720
gataagaacc gagggaaaag tgacaatgtt ccaagcgagg aagtcgtaaa gaaaatgaag   3780
aactattggc ggcagctcct aaatgcgaaa ctgataacgc aaagaaagtt cgataactta   3840
actaaagctg agaggggtgg cttgtctgaa cttgacaagg ccggatttat taaacgtcag   3900
ctcgtggaaa cccgccaaat cacaaagcat gttgcacaga tactagattc ccgaatgaat   3960
acgaaatacg acgagaacga taagctgatt cgggaagtca aagtaatcac tttaaagtca   4020
aaattggtgt cggacttcag aaaggatttt caattctata aagttaggga gataaataac   4080
taccaccatg cgcacgacgc ttatcttaat gccgtcgtag ggaccgcact cattaagaaa   4140
tacccgaagc tagaaagtga gtttgtgtat ggtgattaca aagtttatga cgtccgtaag   4200
atgatcgcga aaagcgaaca ggagataggc aaggctacag ccaaatactt cttttattct   4260
aacattatga atttctttaa gacggaaatc actctggcaa acggagagat acgcaaacga   4320
cctttaattg aaaccaatgg ggagacaggt gaaatcgtat gggataaggg ccgggacttc   4380
gcgacggtga gaaaagtttt gtccatgccc caagtcaaca tagtaaagaa aactgaggtg   4440
```

-continued

```
cagaccggag ggttttcaaa ggaatcgatt cttccaaaaa ggaatagtga taagctcatc   4500
gctcgtaaaa aggactggga cccgaaaaag tacggtggct tcgatagccc tacagttgcc   4560
tattctgtcc tagtagtggc aaaagttgag aagggaaaat ccaagaaact gaagtcagtc   4620
aaagaattat tggggataac gattatggag cgctcgtctt ttgaaaagaa ccccatcgac   4680
ttccttgagg cgaaaggtta caaggaagta aaaaaggatc tcataattaa actaccaaag   4740
tatagtctgt ttgagttaga aaatggccga aaacggatgt tggctagcgc cggagagctt   4800
caaaagggga acgaactcgc actaccgtct aaatacgtga atttcctgta tttagcgtcc   4860
cattacgaga agttgaaagg ttcacctgaa gataacgaac agaagcaact tttgttgag    4920
cagcacaaac attatctcga cgaaatcata gagcaaattt cggaattcag taagagagtc   4980
atcctagctg atgccaatct ggacaaagta ttaagcgcat acaacaagca cagggataaa   5040
cccatacgtg agcaggcgga aaatattatc catttgttta ctcttaccaa cctcggcgct   5100
ccagccgcat tcaagtattt tgacacaacg atagatcgca aacgatacac ttctaccaag   5160
gaggtgctag acgcgacact gattcaccaa tccatcacgg gattatatga aactcggata   5220
gatttgtcac agcttggggg tgactctggt ggttctacta atctgtcaga tattattgaa   5280
aaggagaccg gtaagcaact ggttatccag gaatccatcc tcatgctccc agaggaggtg   5340
gaagaagtca ttgggaacaa gccggaaagc gatatactcg tgcacaccgc ctacgacgag   5400
agcaccgacg agaatgtcat gcttctgact agcgacgccc ctgaatacaa gccttgggct   5460
ctggtcatac aggatagcaa cggtgagaac aagattaaga tgctctctgg tggttctccc   5520
aagaagaaga ggaaagtcta accggtcatc atcaccatca ccattgagtt taaacccgct   5580
gatcagcctc gactgtgcct tctagttgcc agccatctgt tgtttgcccc tcccccgtgc   5640
cttccttgac cctggaaggt gccactccca ctgtcctttc ctaataaaat gaggaaattg   5700
catcgcattg tctgagtagg tgtcattcta ttctgggggg tggggtgggg caggacagca   5760
agggggagga ttgggaagac aatagcaggc atgctgggga tgcggtgggc tctatggctt   5820
ctgaggcgga aagaaccagc tggggctcga taccgtcgac ctctagctag agcttggcgt   5880
aatcatggtc atagctgttt cctgtgtgaa attgttatcc gctcacaatt ccacacaaca   5940
tacgagccgg aagcataaag tgtaaagcct agggtgccta atgagtgagc taactcacat   6000
taattgcgtt gcgctcactg cccgctttcc agtcgggaaa cctgtcgtgc cagctgcatt   6060
aatgaatcgg ccaacgcgcg gggagaggcg gtttgcgtat tgggcgctct tccgcttcct   6120
cgctcactga ctcgctgcgc tcggtcgttc ggctgcggcg agcggtatca gctcactcaa   6180
aggcggtaat acggttatcc acagaatcag gggataacgc aggaaagaac atgtgagcaa   6240
aaggccagca aaaggccagg aaccgtaaaa aggccgcgtt gctggcgttt ttccataggc   6300
tccgcccccc tgacgagcat cacaaaaatc gacgctcaag tcagaggtgg cgaaacccga   6360
caggactata aagataccag gcgtttcccc ctggaagctc cctcgtgcgc tctcctgttc   6420
cgaccctgcc gcttaccgga tacctgtccg cctttctccc ttcgggaagc gtggcgcttt   6480
ctcatagctc acgctgtagg tatctcagtt cggtgtaggt cgttcgctcc aagctgggct   6540
gtgtgcacga accccccgtt cagcccgacc gctgcgcctt atccggtaac tatcgtcttg   6600
agtccaaccc ggtaagacac gacttatcgc cactggcagc agccactggt aacaggatta   6660
gcagagcgag gtatgtaggc ggtgctacag agttcttgaa gtggtggcct aactacggct   6720
acactagaag aacagtattt ggtatctgcg ctctgctgaa gccagttacc ttcggaaaaa   6780
gagttggtag ctcttgatcc ggcaaacaaa ccaccgctgg tagcggtggt ttttttgttt   6840
```

```
gcaagcagca gattacgcgc agaaaaaaag gatctcaaga agatcctttg atcttttcta   6900

cggggtctga cgctcagtgg aacgaaaact cacgttaagg gattttggtc atgagattat   6960

caaaaaggat cttcacctag atccttttaa attaaaaatg aagttttaaa tcaatctaaa   7020

gtatatatga gtaaacttgg tctgacagtt accaatgctt aatcagtgag gcacctatct   7080

cagcgatctg tctatttcgt tcatccatag ttgcctgact ccccgtcgtg tagataacta   7140

cgatacggga gggcttacca tctggcccca gtgctgcaat gataccgcga gacccacgct   7200

caccggctcc agatttatca gcaataaacc agccagccgg aagggccgag cgcagaagtg   7260

gtcctgcaac tttatccgcc tccatccagt ctattaattg ttgccgggaa gctagagtaa   7320

gtagttcgcc agttaatagt ttgcgcaacg ttgttgccat tgctacaggc atcgtggtgt   7380

cacgctcgtc gtttggtatg gcttcattca gctccggttc ccaacgatca aggcgagtta   7440

catgatcccc catgttgtgc aaaaaagcgg ttagctcctt cggtcctccg atcgttgtca   7500

gaagtaagtt ggccgcagtg ttatcactca tggttatggc agcactgcat aattctctta   7560

ctgtcatgcc atccgtaaga tgcttttctg tgactggtga gtactcaacc aagtcattct   7620

gagaatagtg tatgcggcga ccgagttgct cttgcccggc gtcaatacgg gataataccg   7680

cgccacatag cagaacttta aaagtgctca tcattggaaa acgttcttcg gggcgaaaac   7740

tctcaaggat cttaccgctg ttgagatcca gttcgatgta acccactcgt gcacccaact   7800

gatcttcagc atcttttact ttcaccagcg tttctgggtg agcaaaaaca ggaaggcaaa   7860

atgccgcaaa aaagggaata agggcgacac ggaaatgttg aatactcata ctcttccttt   7920

ttcaatatta ttgaagcatt tatcagggtt attgtctcat gagcggatac atatttgaat   7980

gtatttagaa aaataaacaa ataggggttc cgcgcacatt tccccgaaaa gtgccacctg   8040

acgtcgacgg atcgggagat cgatctcccg atcccctagg gtcgactctc agtacaatct   8100

gctctgatgc cgcatagtta agccagtatc tgctccctgc ttgtgtgttg gaggtcgctg   8160

agtagtgcgc gagcaaaatt taagctacaa caaggcaagg cttgaccgac aattgcatga   8220

agaatctgct tagggttagg cgttttgcgc tgcttcgcga tgtacgggcc agatatacgc   8280

gttgacattg attattgact agttattaat agtaatcaat tacggggtca ttagttcata   8340

gcccatatat ggagttccgc gttacataac ttacggtaaa tggcccgcct ggctgaccgc   8400

ccaacgaccc ccgcccattg acgtcaataa tgacgtatgt tcccatagta acgccaatag   8460

ggactttcca ttgacgtcaa tgggtggagt atttacggta aactgcccac ttggcagtac   8520

atcaagtgta tc                                                       8532
```

```
<210> SEQ ID NO 4
<211> LENGTH: 9516
<212> TYPE: DNA
<213> ORGANISM: Artificial
<220> FEATURE:
<223> OTHER INFORMATION: Synthetic construct???3xUGI-rAPOBEC1-SpCas9-
      NLS-UGI-NLS

<400> SEQUENCE: 4
```

```
atatgccaag tacgccccct attgacgtca atgacggtaa atggcccgcc tggcattatg     60

cccagtacat gaccttatgg gactttccta cttggcagta catctacgta ttagtcatcg    120

ctattaccat ggtgatgcgg ttttggcagt acatcaatgg gcgtggatag cggtttgact    180

cacggggatt tccaagtctc caccccattg acgtcaatgg gagtttgttt tggcaccaaa    240

atcaacggga ctttccaaaa tgtcgtaaca actccgcccc attgacgcaa atgggcggta    300
```

```
ggcgtgtacg gtgggaggtc tatataagca gagctggttt agtgaaccgt cagatccgct    360

agagatccgc ggccgctaat acgactcact atagggagag ccgccaccgg gcccatgact    420

aatctgtcag atattattga aaaggagacc ggtaagcaac tggttatcca ggaatccatc    480

ctcatgctcc cagaggaggt ggaagaagtc attgggaaca agccggaaag cgatatactc    540

gtgcacaccg cctacgacga gagcaccgac gagaatgtca tgcttctgac tagcgacgcc    600

cctgaataca agccttgggc tctggtcata caggatagca acggtgagaa caagattaag    660

atgctcccca agaagaagag gaaagtcgag ggcagaggaa gtctgctaac atgcggtgac    720

gtcgaggaga atcctggccc aaccaacctg tccgatatca ttgagaaaga gaccggcaaa    780

cagctggtga tccaggagag catcctgatg ctgcccgaag aggtggagga agtgatcggc    840

aacaagcccg agtccgacat cctggtgcac acagcctatg atgaatccac cgacgagaac    900

gtgatgctgc tgacctccga tgctcccgag tataaaccct gggcactggt gatccaggac    960

tctaatggag agaacaagat caagatgctg cccaagaaga agaggaaagt cgctactaac   1020

ttcagcctgc tgaagcaggc tggagacgtg gaggagaacc ctggacctac aaacctcagt   1080

gacattatcg agaaggaaac aggaaaacag ctcgtcattc aagaatctat tcttatgttg   1140

cctgaggaag tcgaagaggt tattggcaat aaacctgaat ctgatattct tgtccatacc   1200

gcttacgatg agtccacaga tgaaaatgtt atgctgctca catctgacgc accagagtac   1260

aaaccatggg cgctcgttat tcaagattcc aacggcgaaa acaaaatcaa aatgcttccc   1320

aagaagaaga ggaaagtcga aggacggggc tccctcctga cctgtggcga tgtggaagag   1380

aaccccggcc ccatgagctc agagactggc ccagtggctg tggaccccac attgagacgg   1440

cggatcgagc cccatgagtt tgaggtattc ttcgatccga gagagctccg caaggagacc   1500

tgcctgcttt acgaaattaa ttggggggc cggcactcca tttggcgaca tacatcacag    1560

aacactaaca agcacgtcga agtcaacttc atcgagaagt tcacgacaga aagatatttc   1620

tgtccgaaca caaggtgcag cattacctgg tttctcagct ggagcccatg cggcgaatgt   1680

agtagggcca tcactgaatt cctgtcaagg tatccccacg tcactctgtt tatttacatc   1740

gcaaggctgt accaccacgc tgacccccgc aatcgacaag gcctgcggga tttgatctct   1800

tcaggtgtga ctatccaaat tatgactgag caggagtcag gatactgctg gagaaacttt   1860

gtgaattata gcccgagtaa tgaagcccac tggcctaggt atccccatct gtgggtacga   1920

ctgtacgttc ttgaactgta ctgcatcata ctgggcctgc ctccttgtct caacattctg   1980

agaaggaagc agccacagct gacattcttt accatcgctc ttcagtcttg tcattaccag   2040

cgactgcccc cacacattct ctgggccacc gggttgaaaa gcggcagcga gactcccggg   2100

acctcagagt ccgccacacc cgaaagtgat aaaaagtatt ctattggttt agccatcggc   2160

actaattccg ttggatgggc tgtcataacc gatgaataca aagtaccttc aaagaaattt   2220

aaggtgttgg ggaacacaga ccgtcattcg attaaaaaga atcttatcgg tgccctccta   2280

ttcgatagtg gcgaaacggc agaggcgact cgcctgaaac gaaccgctcg gagaaggtat   2340

acacgtcgca agaaccgaat atgttactta caagaaattt ttagcaatga gatggccaaa   2400

gttgacgatt ctttctttca ccgtttggaa gagtccttcc ttgtcgaaga ggacaagaaa   2460

catgaacggc accccatctt tggaaacata gtagatgagg tggcatatca tgaaaagtac   2520

ccaacgattt atcacctcag aaaaaagcta gttgactcaa ctgataaagc ggacctgagg   2580

ttaatctact tggctcttgc ccatatgata aagttccgtg ggcactttct cattgagggt   2640
```

-continued

```
gatctaaatc cggacaactc ggatgtcgac aaactgttca tccagttagt acaaacctat   2700
aatcagttgt ttgaagagaa ccctataaat gcaagtggcg tggatgcgaa ggctattctt   2760
agcgcccgcc tctctaaatc ccgacggcta gaaaacctga tcgcacaatt acccggagag   2820
aagaaaaatg ggttgttcgg taaccttata gcgctctcac taggcctgac accaaatttt   2880
aagtcgaact tcgacttagc tgaagatgcc aaattgcagc ttagtaagga cacgtacgat   2940
gacgatctcg acaatctact ggcacaaatt ggagatcagt atgcggactt atttttggct   3000
gccaaaaacc ttagcgatgc aatcctccta tctgacatac tgagagttaa tactgagatt   3060
accaaggcgc cgttatccgc ttcaatgatc aaaaggtacg atgaacatca ccaagacttg   3120
acacttctca aggccctagt ccgtcagcaa ctgcctgaga aatataagga aatattcttt   3180
gatcagtcga aaaacgggta cgcaggttat attgacggcg gagcgagtca agaggaattc   3240
tacaagttta tcaaacccat attagagaag atggatggga cggaagagtt gcttgtaaaa   3300
ctcaatcgcg aagatctact gcgaaagcag cggactttcg acaacggtag cattccacat   3360
caaatccact taggcgaatt gcatgctata cttagaaggc aggaggattt ttatccgttc   3420
ctcaaagaca atcgtgaaaa gattgagaaa atcctaacct ttcgcatacc ttactatgtg   3480
ggacccctgg cccgagggaa ctctcggttc gcatggatga caagaaagtc cgaagaaacg   3540
attactccat ggaattttga ggaagttgtc gataaaggtg cgtcagctca atcgttcatc   3600
gagaggatga ccaactttga caagaattta ccgaacgaaa aagtattgcc taagcacagt   3660
ttactttacg agtatttcac agtgtacaat gaactcacga aagttaagta tgtcactgag   3720
ggcatgcgta aacccgcctt tctaagcgga gaacagaaga aagcaatagt agatctgtta   3780
ttcaagacca accgcaaagt gacagttaag caattgaaag aggactactt taagaaaatt   3840
gaatgcttcg attctgtcga gatctccggg gtagaagatc gatttaatgc gtcacttggt   3900
acgtatcatg acctcctaaa gataattaaa gataaggact tcctggataa cgaagagaat   3960
gaagatatct tagaagatat agtgttgact cttaccctct ttgaagatcg ggaaatgatt   4020
gaggaaagac taaaaacata cgctcacctg ttcgacgata aggttatgaa acagttaaag   4080
aggcgtcgct atacgggctg gggacgattg tcgcggaaac ttatcaacgg gataagagac   4140
aagcaaagtg gtaaaactat tctcgatttt ctaaagagcg acggcttcgc caataggaac   4200
tttatgcagc tgatccatga tgactcttta accttcaaag aggatataca aaaggcacag   4260
gtttccggac aaggggactc attgcacgaa catattgcga atcttgctgg ttcgccagcc   4320
atcaaaaagg gcatactcca gacagtcaaa gtagtggatg agctagttaa ggtcatggga   4380
cgtcacaaac cggaaaacat tgtaatcgag atggcacgcg aaaatcaaac gactcagaag   4440
gggcaaaaaa acagtcgaga gcggatgaag agaatagaag agggtattaa agaactgggc   4500
agccagatct taaaggagca tcctgtggaa aatacccaat tgcagaacga gaaactttac   4560
ctctattacc tacaaaatgg aagggacatg tatgttgatc aggaactgga cataaaccgt   4620
ttatctgatt acgacgtcga tcacattgta ccccaatcct tttgaagga cgattcaatc   4680
gacaataaag tgcttacacg ctcggataag aaccgaggga aaagtgacaa tgttccaagc   4740
gaggaagtcg taaagaaaat gaagaactat tggcggcagc tcctaaatgc gaaactgata   4800
acgcaaagaa agttcgataa cttaactaaa gctgagaggg gtggcttgtc tgaacttgac   4860
aaggccggat ttattaaacg tcagctcgtg gaaacccgcc aaatcacaaa gcatgttgca   4920
cagatactag attcccgaat gaatacgaaa tacgacgaga acgataagct gattcgggaa   4980
gtcaaagtaa tcactttaaa gtcaaaattg gtgtcggact tcagaaagga ttttcaattc   5040
```

```
tataaagtta gggagataaa taactaccac catgcgcacg acgcttatct taatgccgtc   5100
gtagggaccg cactcattaa gaaatacccg aagctagaaa gtgagtttgt gtatggtgat   5160
tacaaagttt atgacgtccg taagatgatc gcgaaaagcg aacaggagat aggcaaggct   5220
acagccaaat acttctttta ttctaacatt atgaatttct ttaagacgga aatcactctg   5280
gcaaacggag agatacgcaa acgacccttta attgaaacca atggggagac aggtgaaatc   5340
gtatgggata agggccggga cttcgcgacg gtgagaaaag ttttgtccat gccccaagtc   5400
aacatagtaa agaaaactga ggtgcagacc ggagggtttt caaaggaatc gattcttcca   5460
aaaaggaata gtgataagct catcgctcgt aaaaaggact gggacccgaa aaagtacggt   5520
ggcttcgata gccctacagt tgcctattct gtcctagtag tggcaaaagt tgagaaggga   5580
aaatccaaga aactgaagtc agtcaaagaa ttattgggga taacgattat ggagcgctcg   5640
tcttttgaaa agaaccccat cgacttcctt gaggcgaaag gttacaagga agtaaaaaag   5700
gatctcataa ttaaactacc aaagtatagt ctgtttgagt tagaaaatgg ccgaaaacgg   5760
atgttggcta gcgccggaga gcttcaaaag gggaacgaac tcgcactacc gtctaaatac   5820
gtgaatttcc tgtatttagc gtcccattac gagaagttga aaggttcacc tgaagataac   5880
gaacagaagc aactttttgt tgagcagcac aaacattatc tcgacgaaat catagagcaa   5940
atttcggaat tcagtaagag agtcatccta gctgatgcca atctggacaa agtattaagc   6000
gcatacaaca agcacaggga taaacccata cgtgagcagg cggaaaatat tatccatttg   6060
tttactctta ccaacctcgg cgctccagcc gcattcaagt attttgacac aacgatagat   6120
cgcaaacgat acacttctac caaggaggtg ctagacgcga cactgattca ccaatccatc   6180
acgggattat atgaaactcg gatagatttg tcacagcttg gggtgactc tggtggttct   6240
actaatctgt cagatattat tgaaaaggag accggtaagc aactggttat ccaggaatcc   6300
atcctcatgc tcccagagga ggtggaagaa gtcattggga acaagccgga aagcgatata   6360
ctcgtgcaca ccgcctacga cgagagcacc gacgagaatg tcatgcttct gactagcgac   6420
gcccctgaat acaagccttg ggctctggtc atacaggata gcaacggtga gaacaagatt   6480
aagatgctct ctggtggttc tcccaagaag aagaggaaag tctaaccggt catcatcacc   6540
atcaccattg agtttaaacc cgctgatcag cctcgactgt gccttctagt tgccagccat   6600
ctgttgtttg cccctccccc gtgccttcct tgaccctgga aggtgccact cccactgtcc   6660
tttcctaata aaatgaggaa attgcatcgc attgtctgag taggtgtcat tctattctgg   6720
ggggtggggt ggggcaggac agcaaggggg aggattggga agacaatagc aggcatgctg   6780
gggatgcggt gggctctatg gcttctgagg cggaaagaac cagctggggc tcgataccgt   6840
cgacctctag ctagagcttg gcgtaatcat ggtcatagct gtttcctgtg tgaaattgtt   6900
atccgctcac aattccacac aacatacgag ccggaagcat aaagtgtaaa gcctagggtg   6960
cctaatgagt gagctaactc acattaattg cgttgcgctc actgcccgct ttccagtcgg   7020
gaaacctgtc gtgccagctg cattaatgaa tcggccaacg cgcggggaga ggcggtttgc   7080
gtattgggcg ctcttccgct tcctcgctca ctgactcgct gcgctcggtc gttcggctgc   7140
ggcgagcggt atcagctcac tcaaaggcgg taatacggtt atccacagaa tcaggggata   7200
acgcaggaaa gaacatgtga gcaaaaggcc agcaaaaggc caggaaccgt aaaaaggccg   7260
cgttgctggc gtttttccat aggctccgcc cccctgacga gcatcacaaa aatcgacgct   7320
caagtcagag gtggcgaaac ccgacaggac tataaagata ccaggcgttt ccccctggaa   7380
```

```
gctccctcgt gcgctctcct gttccgaccc tgccgcttac cggatacctg tccgcctttc   7440
tcccttcggg aagcgtggcg ctttctcata gctcacgctg taggtatctc agttcggtgt   7500
aggtcgttcg ctccaagctg ggctgtgtgc acgaaccccc cgttcagccc gaccgctgcg   7560
ccttatccgg taactatcgt cttgagtcca acccggtaag acacgactta tcgccactgg   7620
cagcagccac tggtaacagg attagcagag cgaggtatgt aggcggtgct acagagttct   7680
tgaagtggtg gcctaactac ggctacacta gaagaacagt atttggtatc tgcgctctgc   7740
tgaagccagt taccttcgga aaaagagttg gtagctcttg atccggcaaa caaaccaccg   7800
ctggtagcgg tggttttttt gtttgcaagc agcagattac gcgcagaaaa aaaggatctc   7860
aagaagatcc tttgatcttt tctacggggt ctgacgctca gtggaacgaa aactcacgtt   7920
aagggatttt ggtcatgaga ttatcaaaaa ggatcttcac ctagatcctt ttaaattaaa   7980
aatgaagttt taaatcaatc taaagtatat atgagtaaac ttggtctgac agttaccaat   8040
gcttaatcag tgaggcacct atctcagcga tctgtctatt tcgttcatcc atagttgcct   8100
gactccccgt cgtgtagata actacgatac gggagggctt accatctggc cccagtgctg   8160
caatgatacc gcgagaccca cgctcaccgg ctccagattt atcagcaata aaccagccag   8220
ccggaagggc cgagcgcaga agtggtcctg caactttatc cgcctccatc cagtctatta   8280
attgttgccg ggaagctaga gtaagtagtt cgccagttaa tagtttgcgc aacgttgttg   8340
ccattgctac aggcatcgtg gtgtcacgct cgtcgtttgg tatggcttca ttcagctccg   8400
gttcccaacg atcaaggcga gttacatgat cccccatgtt gtgcaaaaaa gcggttagct   8460
ccttcggtcc tccgatcgtt gtcagaagta agttggccgc agtgttatca ctcatggtta   8520
tggcagcact gcataattct cttactgtca tgccatccgt aagatgcttt tctgtgactg   8580
gtgagtactc aaccaagtca ttctgagaat agtgtatgcg gcgaccgagt tgctcttgcc   8640
cggcgtcaat acgggataat accgcgccac atagcagaac tttaaaagtg ctcatcattg   8700
gaaaacgttc ttcggggcga aaactctcaa ggatcttacc gctgttgaga tccagttcga   8760
tgtaacccac tcgtgcaccc aactgatctt cagcatcttt tactttcacc agcgtttctg   8820
ggtgagcaaa aacaggaagg caaaatgccg caaaaaaggg aataagggcg acacggaaat   8880
gttgaatact catactcttc ctttttcaat attattgaag catttatcag ggttattgtc   8940
tcatgagcgg atacatattt gaatgtattt agaaaaataa acaaataggg gttccgcgca   9000
catttccccg aaaagtgcca cctgacgtcg acggatcggg agatcgatct cccgatcccc   9060
tagggtcgac tctcagtaca atctgctctg atgccgcata gttaagccag tatctgctcc   9120
ctgcttgtgt gttggaggtc gctgagtagt gcgcgagcaa aatttaagct acaacaaggc   9180
aaggcttgac cgacaattgc atgaagaatc tgcttagggt taggcgtttt gcgctgcttc   9240
gcgatgtacg ggccagatat acgcgttgac attgattatt gactagttat taatagtaat   9300
caattacggg gtcattagtt catagcccat atatggagtt ccgcgttaca taacttacgg   9360
taaatggccc gcctggctga ccgcccaacg acccccgccc attgacgtca ataatgacgt   9420
atgttcccat agtaacgcca atagggactt tccattgacg tcaatgggtg gagtatttac   9480
ggtaaactgc ccacttggca gtacatcaag tgtatc                             9516
```

<210> SEQ ID NO 5
<211> LENGTH: 23
<212> TYPE: DNA
<213> ORGANISM: Artificial
<220> FEATURE:
<223> OTHER INFORMATION: Synthetic oligonucleotide: hPD1 Sg-1

<400> SEQUENCE: 5
ctacaactgg gctggcggcc agg 23

<210> SEQ ID NO 6
<211> LENGTH: 23
<212> TYPE: DNA
<213> ORGANISM: Artificial
<220> FEATURE:
<223> OTHER INFORMATION: Synthetic oligonucleotide: hPD1 Sg-2

<400> SEQUENCE: 6
cagcaaccag acggacaagc tgg 23

<210> SEQ ID NO 7
<211> LENGTH: 23
<212> TYPE: DNA
<213> ORGANISM: Artificial
<220> FEATURE:
<223> OTHER INFORMATION: Synthetic oligonucleotide: hPD1 Sg-3

<400> SEQUENCE: 7
cggccagttc caaaccctgg tgg 23

<210> SEQ ID NO 8
<211> LENGTH: 23
<212> TYPE: DNA
<213> ORGANISM: Artificial
<220> FEATURE:
<223> OTHER INFORMATION: Synthetic oligonucleotide: hLAG3 Sg-1

<400> SEQUENCE: 8
ccagaccata ggagagatgt ggg 23

<210> SEQ ID NO 9
<211> LENGTH: 23
<212> TYPE: DNA
<213> ORGANISM: Artificial
<220> FEATURE:
<223> OTHER INFORMATION: Synthetic oligonucleotide: hLAG3 Sg-2

<400> SEQUENCE: 9
ccataggaga gatgtgggag gct 23

<210> SEQ ID NO 10
<211> LENGTH: 23
<212> TYPE: DNA
<213> ORGANISM: Artificial
<220> FEATURE:
<223> OTHER INFORMATION: Synthetic oligonucleotide: hLAG3 Sg-3

<400> SEQUENCE: 10
ccggcggcgc cctcctcctg ggg 23

<210> SEQ ID NO 11
<211> LENGTH: 23
<212> TYPE: DNA
<213> ORGANISM: Artificial
<220> FEATURE:
<223> OTHER INFORMATION: Synthetic oligonucleotide: htigit Sg-1

<400> SEQUENCE: 11
gatcgagtgg ccccaggtcc cgg 23

<210> SEQ ID NO 12

<211> LENGTH: 23
<212> TYPE: DNA
<213> ORGANISM: Artificial
<220> FEATURE:
<223> OTHER INFORMATION: Synthetic oligonucleotide: hVISTA Sg-1

<400> SEQUENCE: 12 cettctacaa gacgtggtac cgc 23

<210> SEQ ID NO 13
<211> LENGTH: 23
<212> TYPE: DNA
<213> ORGANISM: Artificial
<220> FEATURE:
<223> OTHER INFORMATION: Synthetic oligonucleotide: 2B4 Sg-1

<400> SEQUENCE: 13
gcagctcagc agcaggacag tgg 23

<210> SEQ ID NO 14
<211> LENGTH: 23
<212> TYPE: DNA
<213> ORGANISM: Artificial
<220> FEATURE:
<223> OTHER INFORMATION: Synthetic oligonucleotide: hCD160 Sg-1

<400> SEQUENCE: 14
aaaacagctg agacttaaaa ggg 23

<210> SEQ ID NO 15
<211> LENGTH: 23
<212> TYPE: DNA
<213> ORGANISM: Artificial
<220> FEATURE:
<223> OTHER INFORMATION: Synthetic oligonucleotide: mTIM3 Sg-1

<400> SEQUENCE: 15
cctcgtgccc gtctgctggg gca 23

<210> SEQ ID NO 16
<211> LENGTH: 22
<212> TYPE: DNA
<213> ORGANISM: Artificial
<220> FEATURE:
<223> OTHER INFORMATION: Synthetic oligonucleotide: mLAG3 Sg-1

<400> SEQUENCE: 16
ccagaccata ggagagatgt gg 22

<210> SEQ ID NO 17
<211> LENGTH: 23
<212> TYPE: DNA
<213> ORGANISM: Artificial
<220> FEATURE:
<223> OTHER INFORMATION: Other information: hPD1 Sg-1 Mut

<400> SEQUENCE: 17
ctataactgg gctggcggcc agg 23

<210> SEQ ID NO 18
<211> LENGTH: 23
<212> TYPE: DNA
<213> ORGANISM: Artificial
<220> FEATURE:
<223> OTHER INFORMATION: Other information: hPD1 Sg-2 Mut

<400> SEQUENCE: 18
cagtaaccag acggacaagc tgg 23

<210> SEQ ID NO 19
<211> LENGTH: 23
<212> TYPE: DNA
<213> ORGANISM: Artificial
<220> FEATURE:
<223> OTHER INFORMATION: Other information: hPD1 Sg-3 Mut

<400> SEQUENCE: 19
cggctagttc caaaccctgg tgg 23

<210> SEQ ID NO 20
<211> LENGTH: 23
<212> TYPE: DNA
<213> ORGANISM: Artificial
<220> FEATURE:
<223> OTHER INFORMATION: Other information: hLAG3 Sg-1 Mut

<400> SEQUENCE: 20
ccagaccata ggagagatgt gag 23

<210> SEQ ID NO 21
<211> LENGTH: 23
<212> TYPE: DNA
<213> ORGANISM: Artificial
<220> FEATURE:
<223> OTHER INFORMATION: Other information: hLAG3 Sg-2 Mut

<400> SEQUENCE: 21
ccataggaga gatgtgagag gct 23

<210> SEQ ID NO 22
<211> LENGTH: 23
<212> TYPE: DNA
<213> ORGANISM: Artificial
<220> FEATURE:
<223> OTHER INFORMATION: Other information: hLAG3 Sg-3 Mut

<400> SEQUENCE: 22
ccggcggcgc cctcctcctg agg 23

<210> SEQ ID NO 23
<211> LENGTH: 23
<212> TYPE: DNA
<213> ORGANISM: Artificial
<220> FEATURE:
<223> OTHER INFORMATION: Other information: hTIGIT Sg-1 Mut

<400> SEQUENCE: 23
gattgagtgg ccccaggtcc cgg 23

<210> SEQ ID NO 24
<211> LENGTH: 23
<212> TYPE: DNA
<213> ORGANISM: Artificial
<220> FEATURE:
<223> OTHER INFORMATION: Other information: hVISTA Sg-1 Mut

<400> SEQUENCE: 24
ccttctacaa gacgtgatac cgc 23

<210> SEQ ID NO 25

```
<211> LENGTH: 23
<212> TYPE: DNA
<213> ORGANISM: Artificial
<220> FEATURE:
<223> OTHER INFORMATION: Other information: 2B4 Sg-1 Mut

<400> SEQUENCE: 25

gcagcttagc agcaggacag tgg                                          23


<210> SEQ ID NO 26
<211> LENGTH: 23
<212> TYPE: DNA
<213> ORGANISM: Artificial
<220> FEATURE:
<223> OTHER INFORMATION: Other information: hCD160 Sg-1 Mut

<400> SEQUENCE: 26

aaaatagctg agacttaaaa ggg                                          23


<210> SEQ ID NO 27
<211> LENGTH: 23
<212> TYPE: DNA
<213> ORGANISM: Artificial
<220> FEATURE:
<223> OTHER INFORMATION: Other information: mTIM3 Sg-1 Mut

<400> SEQUENCE: 27

cctcgtgccc gtctgctagg gca                                          23


<210> SEQ ID NO 28
<211> LENGTH: 22
<212> TYPE: DNA
<213> ORGANISM: Artificial
<220> FEATURE:
<223> OTHER INFORMATION: Other information: mLAG3 Sg-1 Mut

<400> SEQUENCE: 28

ccagaccata ggagagatgt ga                                           22
```

GENE KNOCKOUT METHOD BASED ON BASE EDITING AND ITS APPLICATION

TECHNICAL FIELD

The invention relates to a gene knockout strategy. More specifically, it involves a gene knockout method based on base editing and its application.

BACKGROUND

Traditional eukaryotic targeting gene manipulation is achieved through homologous recombination and blastocyst injection of universal embryonic stem cells. Due to the limitation of the establishment of all-around embryonic stem cells, gene targeting transformation is completed mainly on mice (also reported on rats) through the homologous recombination of the universal embryonic stem cells [Capecchi, 2005]. Another approach to targeted gene editing is cloning, that is, the genetic modification and nuclear transplantation of somatic cells. However, there are some defects in the cloning technology [Carter et al., 2002; Zhu et al., 2004]. For example: 1. It is very difficult to differentiate into undifferentiated cells completely after the clone of somatic cells, which affects the development of embryos and causes developmental defects; 2. All genetic materials are mother-sourced only; 3. Low success rate is detected. Therefore, the traditional gene targeting technique restricts the gene knock-out.

Programmable endonuclease technologies include zinc-finger nucleases (ZENs), transcription activator-like effectors nucleases (TALENs) and clustered regulated interspaced short palindromic repeat, CRISPR-associated (CRISPR/Cas9) [Kim and Kim, 2014]. The invention and promotion of such technologies broke the limits of the universal embryonic stem cells, making it possible for different species to operate. Especially, the CRISPR/Cas9 systems, due to its convenience, efficiency and low-cost, swept the world immediately after its appearance, became the latest, fastest developing and most widely used technology in the area of gene editing, and caused a revolution in the field of gene editing accordingly. Nowadays, CRISPR/Cas9 has been successfully used for DNA knockout, knockin, DNA substitution, DNA modification, RNA modification, DNA markers, gene transcription regulation, etc. [Hsu et al., 2014; Komor et al., 2017]. It has been applied to gene editing of multiple species successfully [Barrangou R & Doudna J A, 2016; Komor et al., 2017].

CRISPR/Cas9 mediated gene specificity editing is based on sgRNA (single guided RNA) to locate the shear double-stranded DNA under the guidance of the target sequence complementary Cas9 protein, in order to trigger double—strand breaks, (DSB): in the condition of no template accessed, non-homologous end joining (NHEJ) repair and frameshift mutations should be caused, leading to the knock-out; In the case of a template, the homology-directed repair (HDR) can be triggered by the homologous recombination, leading to the knock-in [Hsu et al., 2014; Kim and Kim, 2014; Komor et al., 2017]. Due to the low efficiency of HDR (integration is rare), and easy generation of random insertion and deletion (indel) under the homologous end joint mechanism, it would lead to the introduction of new base near breaking point and result in an inaccurate gene editing. In addition, CRISPR/Cas9 mediated gene editing has some off-target effects [Gorski et al., 2017].

SUMMARY OF THE INVENTION

One of the aims of this invention is to provide an efficient and accurate gene knockout strategy.

According to the latest study, the Cas9 fusion protein based on CRISPR/Cas9 technology can be used as the Base Editor (BE). These fusion proteins include dCas9 or Cas9 incision enzyme and cytosine deaminase APOBEC1, which converts cytosine (C) into uracil through deamination, without cutting DNA. Then, through DNA replication or repair, uracil is converted to thymine (T). Similarly, it can convert a single base G into A. In particular, the BE3 made of Cas9 incision enzyme and APOBEC1 can significantly increase the efficiency of base editing to 15-75%. Because no DNA cutting is required to cause DSB, the indel formed is less than 1%, and the gene editing is more accurate [Komor et al., 2016]. Moreover, this approach reduces the off-target effect to 10 times less than the natural background, and the genetic editing is more secure [Nishida et al., 2017]. BE3 has been successfully used in in vivo base editing to achieve CT mutation in mice, with an efficiency of 44~57% [Kim K, Ryu S M, Kim S T, et al. Nat Biotechnol 2017; 35:435-437].

Based on the above BE mediated single-base mutation, especially on the accuracy and specificity of BE3 mediated single-base editing, the inventors design a gene knockout strategy: introducing termination codon by CT mutations, such as by having CAA, CAG and CGA mutated to a termination codon TAA, TAG or TGA, or by having TGG mutated into a termination codon TAA, TGA or TAG through GA mutation, in order to terminate the encoding gene translation and realize a gene knockout.

According to the first aspect of the invention, a gene knockout method is provided, which includes:

selecting a 20 bp-NGG target sequence (PAM sequence) of the coding region (CDS) of the gene to be knocked out, so that it contains a a complete target codon CAA, CAG or CGA; and using sgRNA sequence to locate BE3 to the target sequence, to convert the target single-base C of the target codon into T and thus introduce a corresponding termination codon TAA, TAG or TGA in order to realize the knockout, wherein the target single-base C is located on site 1-8 in the sequence (from left side), preferably on site 4 to 8, the interval between the target codon and NGG is 12 to 14 bp, preferably 14 bp, and the upstream base near the target codon cannot be G; and the sgRNA sequence is a 20 bp sequence complementary to the target sequence.

Alternatively, in the method mentioned above, a CCN-20 bp target sequence (PAM) of the coding region of the gene to be knocked out can also be selected to include a complete target codon TGG, and the downstream base (D) near the target codon cannot be C. Accordingly, the target single base G is located on site 1-8 (at the right end) of the target sequence, preferably on site 4-8, and the interval of the target codon and CCN is 12-14 bp, preferably 14 bp.

According to this invention, BE3 may be selected from the group consisting of: rAPOBEC1-SaCas9-NLS-UGI-NLS; 3×UGI-rAPOBEC1-SaCas9-NLS-UGI-NLS; rAPOBEC1-SpCas9-NLS-UGI-NLS; and 3×UGI-rAPOBEC1-SpCas9-NLS-UGI-NLS, preferably from the group consisting of the last two.

According to the present invention, the method can be used to knock out the following eight target genes: human PD1, LAG3, TIGIT, VISTA, 2B4 and CD160, and mouse TIM3 and LAG3. The corresponding sgRNA sequence is complementary with the gene sequences shown in target Sequence one to eight, respectively.

According to the second aspect of the present invention, an application of the method conducted on human PD1, LAG3, TIGIT, VISTA, 2B4 and CD160 gene knockout in cell line HEK293T is provided.

According to the third aspect of the present invention, an application of the method conducted on human PD1, LAG3, TIGIT, VISTA, 2B4 and CD160 gene knockout in human T cells is provided.

According to the fourth aspect of the present invention, separated T cells or cell lines or their subcultures according to the above applications are provided.

According to the fifth aspect of the present invention, a kit for gene knockout including sgRNA (corresponding to the gene to be knoced out), BE3 and corresponding amplification reagents.

Based on base editing techniques developed on CRISPR/Cas9, this invention establishes a more efficient and accurate as well as less off-target gene knockout strategy than CRISPR/Cas9 by creating termination codons through accurate CT or GA single-base mutation.

EMBODIMENTS

Figure 1:
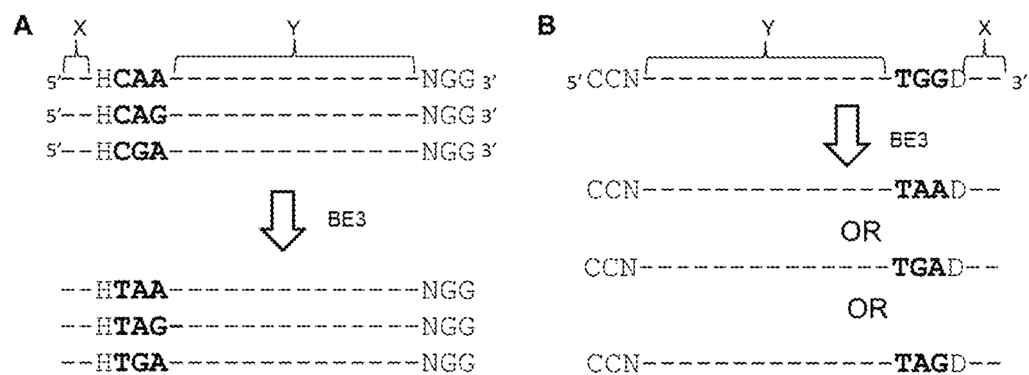
FIG. 1 illustratively shows knocking out the target gene by CT mutation according to the present invention.
Figure 2:
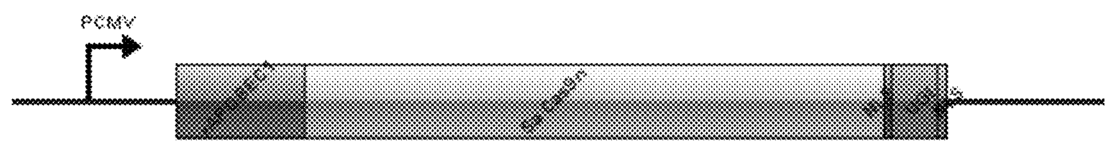
FIGS. 2-5 illustratively show different BE3 structures.
Figure 3:
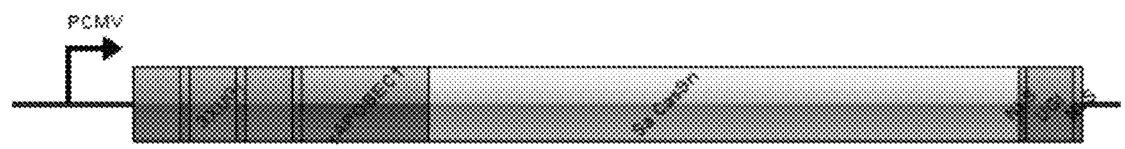
Figure 4:
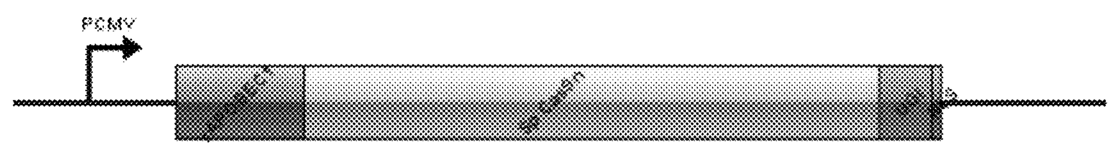
Figure 5:
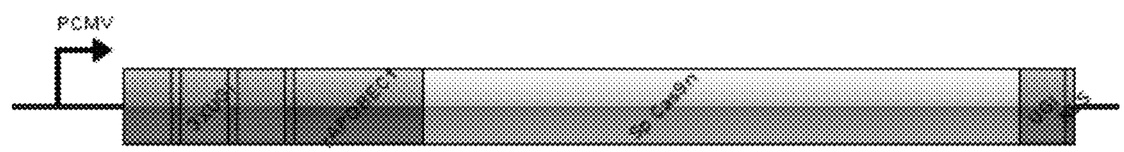

Firstly, different BE3 was constructed, as shown in FIGS. 2-5. After the fusion of different Cas9 nickase and cytosine deaminase (APOBEC1), the following four BE3 were formed:

(1) rapobecl-sacas9-nls-ugi-nls, FIG. 2, SEQ ID NO:1;

(2) 3 xugi-rAPOBEC1-SaCas9-NLS—the UGI-NLS, FIG. 3, SEQ ID NO:2;

(3) rAPOBEC1SpCas9-NLS—the UGI-NLS, FIG. 4, SEQ ID NO:3;

(4) 3 xugi-rAPOBEC1-SpCas9-NLS—the UGI-NLS, FIG. 5, SEQ ID NO:4.

In the following gene knockout, any of the above BE3 can be used, preferably (3) or (4).

Next, in the design of sgRNA, the base point editing is to use sgRNA to locate BE3 or target it to the specific sites. The key of the invention is the selection and design of target gene specific sgRNA. The present invention selects and designs sgRNA as below:

selecting a 20 bp-NGG target sequence (PAM sequence) of the coding region of the gene to be knocked out, such that it includes a complete target codon CAA, CAG or CGA;

the target single base C is preferably located on site 4-8 (in the left end) of the target sequence, the interval between the target codon and NGG is preferably 14 bp, and the upstream base (H) near the target codon cannot be G;

preparing a sequence of 20 bp sgRNA complementary to the target sequence.

Alternatively, a CCN-20 bp target sequence (PAM) of the coding region of the gene to be knocked out is selected to include a complete target codon TGG, and the downstream base (D) near the target codon cannot be C. Accordingly, the target single base G is preferably located on site 4-8 (at the right end) of the target sequence, and the interval of the target codon and CCN is preferably 14 bp. With respct to the 8 different target genes (human PD1, LAG3, TIGIT, VISTA, 2B4 and CD160, and mouse TIM3 and LAG3), the following target gene sequences are selected to design the corresponding sgRNA according to the present invention (the bold and underlined portions represent PAMs; and the italic and underlined portions represent the candidate mutation codes):

1. hPD-1
Sg-1: CTA*CAA*CTGGGCTGGCGGCCAGG

Sg-2: CAG*CAA*CCAGACGGACAAGCTGG

Sg-3: CGGC*CAG*TTCCAAACCCTGGTGG

2. hLAG3
Sg-1: CCAGACCATAGGAGAGATG*TGG*G

Sg-2: CCATAGGAGAGATG*TGG*GAGGCT

Sg-3: CCGGCGGCGCCCTCCTCC*TGG*GG 3. hTIGIT
Sg-1: GAT*CGA*GTGGCCCCAGGTCCCGG

4. hVISTA
Sg-1: CCTTCTACAAGACG*TGG*TACCGC 5. 2B4
Sg-1: GCAGCT*CAG*CAGCAGGACAGTGG

6. hCD160
Sg-1: AAAA*CAG*CTGAGACTTAAAAGGG

7. mTIM3
Sg-1: CCTCGTGCCCGTCTGC*TGG*GGCA 8. mLAG3
Sg-1: CCAGACCATAGGAGAGATG*TGG*

For the above-selected target gene sequences, human PD1 (3), LAG3 (3), TIGIT, VISTA, 2B4 and CD160, and mouse TIM3, LAG3, corresponding sgRNA expression vectors are built and different sgRNAs are imported into pGL3-U6-sgRNA respectively.

Example 1

In the cell line, BE3 mediated base editing is performed, and the termination codon was introduced to realize gene knockout. The knockout of the cell lines is operated regularly (through electrotransfection or liposome transfection), taking liposome transfection for example.

(1) Taking HEK293T cells for example, eukaryotic cells are trained and transfected according to the present invention: HEK293T cells are inoculated and cultured in DMEM sugar culture added by 10% FBS (HyClone, SH30022.01 B), including penicillin (100 U/ml) and streptomycin (100 μg/ml).

(2) Distributing it into a 6-well plate before transfection which is conducted under a density of 70%-80%.

(3) Taking liposome transfection for example. According to manual operation of the Lipofectamine™ 2000 Transfection Reagent (Invitrogen, 11668-019), and taking SpCas9 nickase for example, 2 μg BE3 plasmid and 2 μg pGL3-U6-sgRNA plasmid are evenly blended, and cotransfected into each well. The solution is changed every six to eight hours, and cells are collected after 72 hours.

(4) Analysis of genotype

A, collecting some cells in the pyrolysis liquid (10 μM Tris HCl, 0.4 M NaCl, 2 μM EDTA, 1% SDS) and digesting them by using 100 μg/ml proteinase K. After digestion, phenol-chloroform extraction is made and then dissolved into 50 μl deionized water. B, using a pair of primers N-For and N-Rev for PCR amplification. The PCR recovery product is collected by AxyPrep PCR cleanup purification. 200 ng product is diluted into 20 μl for degeneration and annealing: 95° C., 5 min; 95-85° C. at −2° C./s; 85-25° C. at 0.1° C./s; Hold at 4° C.

C, A base, adenine (A), is added at the end of the PCR recovery product by rTaq. The adenine-added reaction system comprises:

700-800 ng PCR recovery product

5 μl 10×l Buffer (Mg' PLUS)

4 μl dNTP 0.5 μl rTaq (TAKARA, R001 AM)

adding water to obtaion a 50 μl system.

After incubation under 37° C. for 30 minutes, 1 μl product is removed and connected with pMD19-T vector (TAKARA, 3271) to transformate DH5 cells (TransGen, CD201). D, monoclone is selected and the target gene mutation is sequenced with universal primer M13-F. The sequencing results are shown below (the bold and underlined portions represent PAMs; the italics represent mutant codes; and the italic and underlined portions represent mutant bases):

```
1.          hPD-1
Sg-1:       CTACAACTGGGCTGGCGGCCAAG
Mut:        CTATAACTGGGCTGGCGGCCAAG

Sg-2:       CAGCAACCAGACGGACAAGCTGG
Mut:        CAGTAACCAGACGGACAAGCTGG

Sg-3:       CGGCCAGTTCCAAACCCTGGTGG
Mut:        CGGCTAGTTCCAAACCCTGGTGG

2.          hLAG3
Sg-1:       CCAGACCATAGGAGAGATGTGGG
Mut:        CCAGACCATAGGAGAGATGTGAG

Sg-2:       CCATAGGAGAGATGTGGGAGGCT
Mut:        CCATAGGAGAGATGTGAGAGGCT

Sg-3:       CCGGCGGCGCCCTCCTCCTGGGG
Mut:        CCAGCGGCGCCCTCCTCCTGAGG

3.          hTIGIT
Sg-1:       GATCGAGTGGCCCCAGGTCCCGG
Mut:        GATTGAGTGGCCCCAGGTCCCGG

4.          hVISTA
Sg-1:       CCTTCTACAAGACGTGGTACCGC
Mut:        CCTTCTACAAGACGTGATACCGC

5.          2B4
Sg-1:       GCAGCTCAGCAGCAGGACAGTGG
Mut:        GCAGCTTAGCAGCAGGACAGTGG

6.          hCD160
Sg-1:       AAAACAGCTGAGACTTAAAAGGG
Mut:        AAAATAGCTGAGACTTAAAAGGG
```

The results show that the target genes result in the target base mutation of sgRNA, the termination codons are introduced, and the gene knockouts of PD1, LAG3, TIGIT, VISTA, 2B4 and CD160 are achieved successfully.

Example 2

In the primary cells, BE3 mediated base editing was conducted, and the termination codon was introduced to realize gene knockout.

The gene knockout of the primitive cells in human T cells is operated regularly (through electrotransfection or liposome transfection), taking electrotransfection for example.

(1) The Separation and Purification of PBMC Cells:

A, using an anticoagulant tube to collect peripheral blood, with the tube being shaken during the collection so as to have the peripheral blood fully mixed with the anticoagulant;

B, mixing peripheral blood cells and lymphocyte separation medium with equal volume, performing centrifugation, and draining white membrane layer of cells obtained after centrifugation;

C, mixing the white membrane layer of cells with PBS or serum-free cell culture medium 1640 and then performing centrifugation. The precipitation is the PBMC cells.

Repeat three times.

(2) Enrichment of the CD3 Positive Cells

A, adjusting PBMC cells concentration to $50\times10^6$ cell/ml;

B, adding 50 μl CD3+ enriched antibodies cocktail per ml, blending and then standing at room temperature for 5 minutes;

C, adding 150 μl per ml magnet, blending and then standing for 10 minutes at room temperature;

D, placing the centrifugal tube on a magnetic rack and standing for 5 minutes, then draining upper cell suspension into a new 15 ml centrifugal tube.

E, repeat the operation once.

F, performing centrifugation: 300*g at room temperature for 10 minutes and then collecting cells.

G, cell counting.

(3) Electrotransfection of CD3 Positive Cells

A, configure the electrotransfection system

Adding 8 μg BE3 plasmid and 8 μg pGL3-U6-sgRNA plasmid to a 1.5 ml centrifugal tube, then adding 82 μl electrotransfection buffer and 18 μl supplement1 according to the Lonza Amaxa DianZhuan kit specifications, and mixing evenly.

B, collecting $20\times10^6$ cells to a 15 ml centrifugal tube, centrifuging 300 g for 10 minutes, and discarding the supernatant.

C, resuspending cells with the electrotransfection solution made from A, and transferring it to an eletrotransfection cup.

D, Using the instrument Lonza 2B, U-014 procedures for electrotransfection.

E, after electrotransfection, the cells being removed to a preheated AIM-V medium added with 10% FBS quickly, and incubated in 5% CO' incubator at 37° C. for 2 hours.

F, changing the solution for cells after electrotransfection, resuspending the cells with $1\times10^6$/ml cell density, and incubating overnight.

(4) The Activation and Cultivation of T Cells

A, after 24 hours for electrotransfection, adding 100 U/ml IL-2 to the medium, adding CD3/CD28 dynabeads to the proportion of 1:1, and activating T cells.

B, every two days changing half in liquid to the cells, or adding IL-2, so that the cell density is always maintained at 1×106/ml.

C, after being activated for five days the T cells being collected in a 15 ml centrifugal tube which is positioned in a magnetic frame. Slowly removing supernatant to another clean 15 ml centrifugal tube. Repeat this step once.

D, centrifuging 300*g at room temperature for 10 minutes, removing supernatant, and resuspending cells by using 10% FBS, 300 U/ml AIM-IL-2 V medium, with density controlled in 1×106/ml.

E, every two days changing half in liquid to the cells, or adding IL-2, and counting, with cell density always maintained at 1×106/ml.

(5) Analysis of Genotype

A, collecting some cells in the pyrolysis liquid (10 μM Tris HCl, 0.4 M NaCl, 2 μM EDTA, 1% SDS), and digesting them by using 100 μg/ml proteinase K. After digestion, phenol-chloroform extraction is made and then dissolved into 50 μl deionized water.

B, using a pair of primers N-For and N-Rev for PCR amplification. The PCR recovery product is collected by AxyPrep PCR cleanup purification. 200 ng product is diluted to 20 μl for degeneration and annealing: 95° C., 5 min. 95-85° C. at −2° C./s; 85-25° C. at 0.1° C./s; Hold at 4° C.

C, A base, adenine (A), is added at the end of the PCR recovery product by rTaq. The adenine-added reaction system compromises:

700-800 ng PCR recovery product
5 μl 10× Buffer ($Mg^{2+}$+PLUS)
4 μl dNTP
0.5 μl rTaq (TAKARA, R001 AM)
adding water to obtaion a 50 μl system.

After incubation under 37° C. for 30 minutes, 1 μl product is removed and connected with pMD19-T vector (TAKARA, 3271) to transform DH5 competent cells (TransGen, CD201).

D, monoclone is selected, and sequence each T cells target gene mutations with universal primers M13-f. The sequencing results are shown as below (the bold and underlined portions represent PAMs; the italics represent mutant codes; and the italic and underlined portions represent mutant bases):

```
1.        hPD-1
Sg-1:     CTACAACTGGGCTGGCGGCCAGG
Mut:      CTATAACTGGGCTGGCGGCCAGG

Sg-2:     CAGCAACCAGACGGACAAGCTGG
Mut:      CAGTAACCAGACGGACAAGCTGG

Sg-3:     CGGCCAGTTCCAAACCCTGGTGG
Mut:      CGGCTAGTTCCAAACCCTGGTGG

2.        hLAG3
Sg-1:     CCAGACCATAGGAGAGATGTGGG
Mut:      CCAGACCATAGGAGAGATGTGAG

Sg-2:     CCATAGGAGAGATGTGGGAGGCT
Mut:      CCATAGGAGAGATGTGAGAGGCT

Sg-3:     CCGGCGGCGCCCTCCTCCTGGGG
Mut:      CCGGCGGCGCCCTCCTCCTGAGG

3.        hTIGIT
Sg-1:     GATCGAGTGGCCCCAGGTCCCGG
Mut:      GATTGAGTGGCCCCAGGTCCCGG
```

-continued

```
4.        hVISTA
Sg-1:     CCTTCTACAAGACGTGGTACCGC
Mut:      CCTTCTACAAGACGTAGTACCGC

5.        2B4
Sg-1:     GCAGCTCAGCAGCAGGACAGTGG
Mut:      GCAGCTTAGCAGCAGGACAGTGG

6.        hCD160
Sg-1:     AAAACAGCTGAGACTTAAAAGGG
Mut:      AAAATAGCTGAGACTTAAAAGGG
```

The results show that the target genes result in the target base mutation of sgRNA, the termination codons are introduced, and the gene knockouts of PD1, LAG3, TIGIT, VISTA, 2B4 and CD160 are achieved successfully.

Example 3

Developing BE3 Mediated Gene Knockout Mice

Conducting regular operation on mice embryo collection, microinjection of embryo, embryo culture and embryo transfer, etc. For example, the mice were knocked out of TIM3 and LAG3 genes.

(1) Microinjection: the fertilized egg was injected by BE3 mRNA and TIM3 specificity sgRNA (corresponding to SEQ ID NO:15), or by BE3 mRNA and LAG3 specificity sgRNA (corresponding to SEQ ID NO:16) respectively. Conventional embryo transfer was then conducted;

(2) genotype analysis:

genomic DNA is extracted by regular mice tail-cutting, and the coding regions are PCR amplified respectively. Sanger sequencing, with the sequencing result shown as below (the bold and underlined portions represent PAMs; the italics represent mutant codes; and the italic and underlined portions represent mutant bases):

```
7.        mTIM3
Sg-1:     CCTCGTGCCCGTCTGCTGGGGCA
Mut:      CCTCGTGCCCGTCTGCTAGGGCA

8.        mLAG3
Sg-1:     CCAGACCATAGGAGAGATGTGG
Mut:      CCAGACCATAGGAGAGATGTGA
```

The above results demonstrate CT mutation of TIM3 and LAG3 and introduction of termination codon. TIM3 and LAG3 knockout mice have been successfully developed.

The invention claimed is:

1. An ex vivo method of knocking out a human PD1 gene comprising:

selecting a 20 bp-NGG target sequence of the coding region of the gene to be knocked out, such that it contains a complete target codon CAA, CAG or CGA; and using sgRNA sequence to position BE3 Base Editor 3 (BE3) in the target sequence to convert the target single-base C of the target codon into T, in order to introduce a corresponding termination codon TAA, TAG or TGA for realization of the gene knockout, wherein the target single-base C is located between site 1 to 8 of the target sequence; the interval of the target codon and NGG is 12 to 14 bp; the upstream base adjacent the target codon cannot be G;

wherein the human PD1 gene is in a human T cell line, and the sgRNA sequences are complementary to the 20 bp-NGG target sequences and are selected from the group consisting of "cagcaaccag acggacaage tgg" as identified by SEQ ID NO:6 and "cggccagttc caaaccctgg tgg" as identified by SEQ ID NO:7; and wherein BE3 is rAPOBEC 1-SaCas9-NLS-UGI-NLS as identified by the nucleotide of SEQ ID NO:1.

* * * * *